United States Patent [19]

Weiss et al.

[11] 4,072,565

[45] Feb. 7, 1978

[54] PRODUCTION OF VIRUSES IN TISSUE CULTURE WITHOUT USE OF SERUM

[75] Inventors: Stefan Adam Weiss; Harry Lester Torney, both of Carmel; William Joseph Caldwell, Indianapolis, all of Ind.

[73] Assignee: The Dow Chemical Company, Midland, Mich.

[21] Appl. No.: 520,574

[22] Filed: Nov. 4, 1974

[51] Int. Cl.$^2$ ............................ C12B 3/00; C12K 9/00; A61K 39/12

[52] U.S. Cl. ...................................... 195/1.1; 195/1.7; 195/1.8; 424/89

[58] Field of Search ........................ 195/1.1, 1.7, 1.8; 424/89

[56] References Cited

PUBLICATIONS

Chansouria et al.–Quarterly Journal of Surgical Sci., vol. 6, (1970), pp. 113–117.

Higuchi–J. Infect. Dis., vol. 112, (1963), pp. 213–220.
Tribble et al.–J. Infect. Dis., vol. 112, (1963), pp. 221–225.
Tribble et al.–Chem. Abst., vol. 59, (1963), p. 9077c.
Giffiths–Chem. Abst., vol. 74, (1971), p. 72200r.
U.S. Dispensatory–25th Edition, (1955), pp. 688 & 689.
Willmer–Cells and Tissues in Culture, vol. 1, (1965), pp. 103–105 & 593–595.

*Primary Examiner*—Sam Rosen
*Attorney, Agent, or Firm*—Maynard R. Johnson

[57] ABSTRACT

Growth of cells in tissue culture and virus vaccine production in tissue culture in the absence of serum are disclosed. The cells in tissue culture are grown initially in a chemically defined medium containing protamine zinc insulin, and the protamine zinc insulin medium is removed before virus propagation. Supplementation with serum or serum fractions can be eliminated entirely; and improved virus production in a serum free system can be obtained.

15 Claims, No Drawings

PRODUCTION OF VIRUSES IN TISSUE CULTURE WITHOUT USE OF SERUM

BACKGROUND OF THE INVENTION

The present invention is concerned with virus production in tissue culture using a chemically defined medium. The term "chemically defined medium" is used in virology and tissue culture to refer to culture media of known chemical composition, both quantitatively and qualitatively, in contrast to natural or undefined media containing natural products such as animal serum, embryo extracts, yeast hydrolysates, etc. of unknown or incompletely known chemical constitution.

A number of chemically defined media are known. Most of these are solutions of nutrients, e.g., carbohydrates, lipids and amino acids, with vitamins, salts and minerals, and often containing other nutrient materials such as purine bases, adenosine triphosphate, etc.

The media are generally used as a solution in a balanced salt solution ("BSS"), a solution balanced in quantity and ratio of ionic species so as to be physiologically acceptable in pH, mineral content, osmotic pressure, etc. A number of balanced salt solutions are in widespread use, e.g., Hank's BSS Earle BSS; Dulbecco Phosphate Buffered Saline, Puck saline, and others. A number of chemically defined media likewise widely used, e.g., Medium 199 of Morgan, Morton and Parker, Proc. Soc. Exper. Biol. & Med. 73: 1–8 (1950); Eagle Basal Medium, Science 122:501–4 (1955); Science 123: 845–7 (1956); Eagle, et al, J. Biol. Chem. 226: 191–206 (1957); Eagle Minimum Essential Medium, Eagle, Science 130: 432–7 (1959); Trowell Medium T8, Exper. Cell Res. 16: 118–147 (1959); Waymouth MB 752/1 Medium, J. Nat. Cancer Inst. 22: 1003–17 (1959); Puck N 16 Puck, Cieciura et al. J. Exper. Med. 108: 945–956 (1958) and Neuman and Tytell, Proc. Soc. Exptl. Biol. Med., 104: 252–256 (1960). Details for preparation and formulation of such media are found in conventional reference texts, such as Handbook of Cell and Organ Culture, by Merchant, Kahn and Murphy, Burgess Publ. Co., Minneapolis (1960); and In Vitro Monograph No. 1, A Survey of Commercially Available Tissue Culture Media, by Helen C. Morton, In Vitro (J. Tissue Culture Association), Vol. 6, No. 2, pp. 89–108 (1970).

In addition to classification of media as "defined" or "undefined" media, they are also classified broadly on the basis of ability to support cell metabolism and proliferation. Media which permit metabolism of cells at levels adequate for many purposes, including virus production, but which either do not support significant cellular proliferation at all or which support only marginal limited proliferation, are referred to as "maintenance media". Media which support cellular proliferation are generally referred to as "growth media". Most growth media have as their base a BSS or a chemically defined medium which is supplemented with one or more natural products, usually animal serum. Typical growth media include either Eagle's Basal Medium or Medium 199 supplemented with 10 to 20 percent whole animal serum, BSS with 40 percent serum; and 40 percent BSS with 40 percent serum and 20 percent embryo extract. Some chemically defined protein-free media can be used as growth media for a limited number of cell lines. Katsuta and Takaoka, Methods in Cell Biology VI, Ed. by Prescott, Academic Press (1973) Chapter 1. However, for growth of primary cells in tissue culture, and for most large scale tissue culture for vaccine production, a serum supplement has been necessary.

The disadvantages of using serum in vaccine production are well known. Suitable serum is difficult and expensive to obtain, store and use; it is a source of undesirable foreign proteins which may be carried into the final vaccine product; its composition varies from lot to lot; and it is a potential source of contaminating viruses or Mycoplasma. Esber et al., J. National Cancer Institute, 50: 559–62 (1973), Barile and Kerne, Proc. Soc. Exp. Biol. Med. 138: 432–7 (1971); Merril et al., In Vitro, 8: 91–3 (1972).

DESCRIPTION OF PRIOR ART

The present invention utilizes a medium containing insulin. Various media containing insulin are known and have been used. The growth media containing serum generally contain some insulin, naturally present in the serum in uncontrollable, variable amounts. Other media include Trowell T-8, supra, the "Serum Free Medium" of Neuman and Tytell, supra, the medium of Frenkel, Am. J. Vet. Res., Vol. XI, 371–373 (1950) and Vol. XII, 187–90 (1951), and Waymouth MAB 87/3, Tissue Culture, Ramakrishnan ed., Junk, The Hague (1965) p. 168. See also U.S. Pat. Nos. 3,196,077 and 3,655,873, and Katsuka and Takaoka, Supra, Table II.

Frenkel's medium contains about 0.9 units insulin per liter; Trowell's medium contains about 50 milligrams per liter and contains minimal zinc; Waymouth's contains 8 milligrams per liter. The Neuman and Tytell medium contains one milligram insulin per liter. (One milligram insulin corresponds to over 20 units, British Pharmacopoeia, 1973, 246). While such media have had various applications, they have not been entirely satisfactory for large scale applications such as vaccine production or large scale primary tissue culture.

Protamine zinc insulin (from time to time abbreviated as "PZI" herein) is generally available as a sterile solution in aqueous buffer of insulin modified by zinc chloride and protamine. The protamine zinc insulin suspension contains from about 0.2 to about 0.25 milligrams zinc and from about 1.0 to about 1.7 milligrams protamine for each 100 insulin units, and the suspension has a pH of from about 6.9–7.4. (See, e.g., United States Pharmacopeia, XVIII, (1970) pp 335–6; British Pharmacopeia, 1973, 246). The material is commercially available in a form suitable for injection into humans, and this form is preferably used in the invention. Protamine zinc insulin is known to differ markedly in its biological action from other forms of insulin, Remington's Pharmaceutical Sciences, Thirteenth Ed., Mack Pub. Co. Easton, Pa. Chapter 62, pp. 1048–9 (1965). See also Merck Index, Eighth Ed., Merck & Co., Inc, Rahway, N.J. p. 879 (1968), J. Pharmacol. Exptl. Therap. 58, 78 (1936) and U.S. Pat. No. 2,143,591 and 2,179,384.

SUMMARY OF THE INVENTION

The present invention is concerned with tissue culture and virus propagation in tissue culture, and is particularly concerned with tissue culture and virus propagation in chemically defined media. More particularly the invention concerns tissue culture and virus propagation in tissue culture in which animal cells are grown in tissue culture using a tissue culture maintenance medium which comprises a small growth enhancing amount of protamine zinc insulin. The invention also includes a novel medium comprising a growth enhancing amount protamine zinc insulin, and a vaccine produced by the method.

It has now been discovered that the addition of protamine zinc insulin to tissue culture media, particularly chemically defined media, provides unexpected beneficial results in terms of enhanced cell attachment, enhanced cell growth both qualitatively and quantitatively, increased life of tissue culture cell monolayers in excellent condition; and improvements in virus vaccine production in such tissue culture cells. The invention provides production of animal cells and virus vaccines in tissue culture in the complete absence of chemically undefined supplements such as animal serum, embryo extracts and the like, and provides consistently improved results suitable for commercial production operations.

The medium of the invention is a sterile, chemically-defined, tissue culture maintenance medium which comprises protamine zinc insulin (hereinafter abbreviated "PZI") dispersed therein in an amount effective to significantly enhance cell growth in tissue culture. The optimum amount of PZI to be added in particular situations can vary according to factors such as type of cells, type of chemically defined medium, pH (which also affects solubility of PZI), incubation conditions, etc. In particular cases the amounts to be employed for best results can be readily ascertained by classical range finding procedures for studing statistically significant growth enhancement. For example, comparison of media with differing levels of PZI to the maintenance medium alone can be used. In general, enhanced growth is obtained with PZI concentrations from about 0.05 to about 0.5 units PZI per milliliter of final tissue culture medium. Substantially lower amounts of PZI, e.g., 0.01 units/liter are generally insufficient to enhance growth, and substantially higher amounts, e.g., 0.7 units or more per milliliter, generally give no additional enhancement and the additional excess PZI can be detrimental. PZI concentration of from about 0.075 to about 0.1 to about 0.2 to about 0.3 units per milliliter are preferred.

In one embodiment, the medium also comprises a supplemental growth enhancing amount of glucose in addition to PZI. The supplemental amount of glucose used is generally that amount necessary to make the final glucose concentration (including glucose in the maintenance medium as well as the supplement) from about 1150 to about 2000 milligrams per liter or more. In another embodiment, the medium contains a minor amount of pyruvate, about 5.50 micrograms per milliliter.

The maintenance medium can be any tissue culture maintenance medium such as Medium 199, Eagles Basal Medium, Eagle's Minimum Essential Medium, etc.; the many modifications of such media, or a specially formulated medium. While it is essential that the medium be one which provides sufficient nutrients, (salts, vitamins, carbohydrates, lipid, amino acids, etc.) to permit continued cell metabolism, although it is not essential that the medium support rapid cell proliferation of the cells in question. That is, the medium, without PZI, should itself be sufficient to function as a maintenance medium for the cells in question, although it need not be sufficient to serve alone as a growth medium for the same cells. The medium can also be one sufficient to support growth, in which case the invention provides improved results. It should contain less than about 0.05 units per milliliter of insulin-containing material other than PZI, and preferably contains PZI as the sole essential detectable insulin source.

Although the invention is operable with a chemically-undefined medium, many of the advantages provided by the invention will be sacrificed or obscured. For example, the advantages of cell and virus production in a chemically-defined system, are inconsistent with the use of undefined substances such as serum. Accordingly, the medium should be one which is free of biological fluids of chemically undefined composition, such as serum, plasma, amniotic fluid, embryo extracts, etc., and should preferably be a chemically-defined medium. The chemical identity and amount of all ingredients in the medium will then be predetermined.

In formulating the medium of the invention, the PZI is added to the maintenance medium ingredients in any convenient manner suitable to disperse the PZI throughout the medium, it being understood that sterility is maintained and conditions capable of denaturing the PZI are avoided. In a convenient and preferred procedure, a chemically-defined maintenance medium is formulated, sterilized by autoclaving, sterile filtration or both, and the PZI is added in the form of the aqueous buffer USP in injectable suspension. The addition is conveniently carried out by adding the PZI suspension to about 5 to 15 volumes of the medium, stirring the mixture for a few hours (e.g. 1–3 hours) at temperatures from about 20°–40° C., then adding additional maintenance medium thereto to obtain the final composition for use.

The new medium is used according to the invention by inoculating the medium of the invention with cells to be grown in tissue culture, and incubating the cells and medium under conditions conductive to cell growth in tissue culture. The incubation is normally carried out under conditions of pH, (generally 7.1 or 7.2 to 7.5 or 7.6) temperature, (generally about 28° C.–40° C., preferably about 35°–38° C.) irradiation, asepsis, oxygenation, etc. known to be suitable for the type of cells used. The incubation can be carried out in any suitable vessel, including glass bottles and glass non-toxic metal or organic polymer plastic bottles or tissue culture propagators. Rapid cell attachment is obtained, generally with at least 50–70 percent of the cells attaching to the vessel surface after 15–30 minutes incubation. Excellent and rapid proliferation is generally evident within two to five days after seeding, i.e. beginning the incubation.

When viruses are to be propagated, as in virus vaccine production, the incubation of cells and medium with PZI is continued until a predetermined desired degree of cell growth is obtained (e.g., end of the "log phase" of cell growth, achievement of 90–100 percent confluency of cell monolayers etc.). The medium with PZI is then removed by conventional procedures such as decantation, aspiration or the like, and replaced by a chemically-defined maintenance medium which does not contain PZI; the cells are inoculated with seed virus; the cells, virus and PZI-free maintenance medium are incubated under conditions conductive to virus propagation until substantial propagation of virus has occurred; and the virus is then harvested according to conventional procedures.

Removal of the PZI containing medium at the time of virus seeding minimizes risks of cell over proliferation, and also reduces the amount of PZI remaining to be carried into the final virus vaccine product. Although the replacement medium can be characterized as "PZI-free", it is understood that some PZI will generally remain with the cells through virus production. The remaining PZI concentration is generally below the levels which would have any significant deleterious effect on administration of a virus vaccine; and it can be reduced further by washing or rinsing the cells with fresh PZI-free medium prior to addition of the replacement medium and seed virus. In general, the PZI concentration will be a minor amount ranging from below the amount quantifiable by radioimmunoassay (and thus below normal minimum human serum levels about 4 microunits or 0.000,004 units per milliliter) to amounts from about 0.05 to about 0.5 units per milliliter in the freshly prepared PZI medium, decreasing by about 25–75 percent after 24–72 hours of cell growth; decreasing again to from minimum below quantifiable levels to from about 50 to about 400 to about 1000 microunits (0.000,050 to 0.0004 units) per milliliter during virus propagation and harvest.

Vaccine produced in the process of the invention, with or without washing the cells after removal of PZI medium, and before virus seeding can contain from about 4 or less to about 1000 microunits of PZI per milliliter. Although this concentration range extends above the normal human serum levels of insulin (about 4–25 microunits per milliliter), it is far below the concentrations present in suspensions of PZI for injection 40, 80 or 100 units per milliliter, and is insufficient to exhibit significant physiological effects when used in an injectable vaccine. Virus vaccines produced by the process of the invention preferably contain, in addition to an effective immunizing dose of the virus, the physiologically-acceptable harvest residue of tissue culture cells and maintenance medium, and optional added stabilizers or adjuvants, an amount of PZI from that amount detectable by radioimmonoassay or equivalent procedure to a maximum concentration physiologically acceptable for injection without significant deleterious physiological effects ascribable to the PZI. The concentration is conveniently between about 4 or less and 1000 microunits PZI per milliliter of final dosage form vaccine.

Virus vaccines produced according to the invention comprise (1) the virus, generally a live attenuated virus capable immunizing susceptible subjects without causing significant symptoms of the disease being immunized against or a significant degree of side effects; (2) optional pharmaceutically acceptable adjuvants such as buffers, stabilizers such as lactose-glutamate (U.S. Pat. No. 3,133,861), sugar, albumin or glutamine phosphate (U.S. Pat. Nos. 3,401,084 and 3,555,149) and, when ready for injection, a pharmaceutically-acceptable fluid for injection such as sterile pyrogen-free water, or isotonic salt solution; and (3) a pharmaceutically-acceptable harvest residue resulting from the production and harvesting of the vaccine. The harvest residue is generally a chemically-undefined mixture containing metabolized ingredients from the tissue culture maintenance medium used during virus production; cell metabolic products; a minor amount of cellular debris which is not removed by vaccine harvesting and clarification techniques; and residual insulin remaining from the initial growth of the cells in the PZI medium. The vaccine of the invention is essentially free of exogenous chemically-undefined material. That is, the vaccine contains no analytically detectable chemically-undefined biological material other than that resulting from growth and metabolism of the cells and from virus replication. E.g., a vaccine produced in chick embryo tissue culture will be free of detectable bovine serum components.

It will be apparent from the foregoing that the present invention can be readily adapted to production of vaccines and cells in tissue culture in a wide variety of situations, using conventional procedures in the tissue culture and vaccine art. The invention is particularly well suited to production of novel live virus vaccine compositions containing residual PZI as indicated above, and is adaptable to use in both mammalian and avian cell systems. Further description in detail is provided below.

DETAILED DESCRIPTION OF THE INVENTION

The following series of Examples illustrate the application of the invention using primary chick embryo cells in tissue culture and live attenuated rubeola virus (Schwarz strain) as the virus vaccine. Additional Examples illustrate other cells-duck embryo, rabbit kidney, monkey kidney; and other viruses-mumps, rubella, polio, etc. In the Examples, the complete Medium 199 ("M-199") of Morgan, Morton and Parker, Proc. Soc. Exp. Biol. & Med. 73: 1–8 (1950), with Hank's BSS is generally employed as the chemically-defined maintenance medium. The chick embryo tissue culture cells are prepared from eggs free of RIF (Rous interfering factor) according to classical techniques; e.g., removal of eyes, beaks and rear limbs; washing; mincing; trypsinizing; filtering; centrifuging to separate cells from trypsin solution, and suspending cells in fresh medium. Other cell systems are prepared by classical techniques. Since both the cell and medium preparation techniques are well known, they are not described here in detail.

EXAMPLE 1 — CELL PLANTING AND GROWTH

A cell suspension was prepared using 12 day old chick embryos, trypsinized 2 hours at 37° C., and suspended in Hank's balanced salt solution at a concentration of about $3 \times 10_5$ cell per milliliter. A series of 32 fluid ounce glass tissue culture bottles was prepared. To each bottle is added 75 milliliters of sterile M-199. Various test supplements were added to different test groups of bottles, three bottles per group, and the bottles were then seeded with the cell suspension. The cells were incubated at 36.5°–37° C. After 48 hours, medium was decanted and replaced with fresh M-199 with Hank's BSS, but without test supplement. The cells were observed daily. The general appearance of the cells (e.g., – "E" – excellent, "G" – good, "F" – fair, "P" – poor, etc.) and extent of the confluent monolayer in percentage of surface covered are recorded below:

| TEST SUPPLEMENT | RESULTS AFTER DAYS INCUBATION | | | | | | | | |
|---|---|---|---|---|---|---|---|---|---|
| | 1 | 2 | 3 | 4 | 5 | 6 | 7 | 8 | 9 |
| None - M-199 alone | G/30 | G/30 | F/40 | F/50 | F/60 | F-G/70 | G/90 | G/90 | E/100 |
| 2% Fetal Calf Serum | G/50 | G/70 | G/90 | E/100 | E/100 | E/100 | E/100 | E/100* | E/100* |
| Protamine Zinc Insulin (PZI 0.2 units/milliliter | G/50 | G/70 | G-E/90 | E/100 | E/100 | E/100 | E/100 | E/100 | E/100 |
| PZI 0.2 u/ml. plus 0.2 u/ml. added on day 2 | | G/70 | F/80 | G/80 | F/80 | F/80 | F-G/90 | F-G/90 | F-G/90 |

-continued

| TEST SUPPLEMENT | RESULTS AFTER DAYS INCUBATION | | | | | | | | |
|---|---|---|---|---|---|---|---|---|---|
| | 1 | 2 | 3 | 4 | 5 | 6 | 7 | 8 | 9 |
| None | F/20 | F/30 | F/30 | F/30 | F/50 | F/60 | F/70 | F/70 | |
| 2% Fetal Calf serum | G/60 | G/70 | E/95 | E/100 | | | | E/100* | |
| PZI 0.2 u/ml. | G/50 | G/70 | G/90 | G/95 | E/100 | E/100 | E/100 | E/100 | |
| Insulin 0.2 u/ml. | F/20 | F/30 | G/40 | G/50 | G/70 | G/70 | G/75 | G/90 | |

*Retraction (Separation of cell monolayer from tissue culture bottle surface.)
The first four series were seeded with 1.5 ml. cell suspension per bottle. The second four were seeded 24 hours later with 2.0 ml. of the same suspension per bottle.
The above results illustrate the improvement in cell growth according to the invention, both in early attainment of excellent complete confluent monolayers, and in maintenance of the monolayer for several days without retraction. They also indicate the improvement with respect to M-199 alone, or M-199 with regular insulin.

EXAMPLE 2

In a procedure similar to that of Example 1, a series of culture bottles were prepared, each containing 75 milliliters of M-199. Various supplements were added to test groups of bottles, then the test media were seeded with 1.7 milliliters per bottle of chick embryo cell suspension containing $3 \times 10^5$ cells per milliliter. The resulting bottles were incubated at 37° C. and observed daily for 10 days, then at longer intervals for another 10 days.

M-199 with 0.1 percent glucose showed slow growth, with ratings of G/30 and F/30 on days 1 and 2, increasing to E/90 on day 9 and reaching E/100 on days 12, 14 and 20. M-199 with 2 percent fetal calf serum was rated E/90 on the third day, E/100 on days 4 through 8, with cell retraction beginning on day 9 and sloughing of cells from the bottle surface too extensive to permit grading on days 12, 14 and 20.

M-199 with 10 units protamine zinc insulin ("PZI") per bottle (0.13 units PZI per milliliter) and 0.25 percent added glucose by weight gave excellent results, being rated E/100 beginning on day 4 (as early as 2–3 days in some bottles) and continuing throughout the entire test. An identical medium containing 0.267 units PZI per ml. and 0.25 percent glucose was rated G/100 on days 5–7, and E/100 on day 8 and thereafter. With 0.40 units PZI per ml. and 0.25 percent added glucose, the rating was G/100 for days 5–7; G-E/100 for days 8–10, 12 and 14; and dropping to F-G/90 on day 20. With 0.53 units PZI per ml. and 0.25 percent added glucose, the rating was F/100 on day 5, improving to G/100 on days 6–10, 12 and 14 and dropping on day 20 to G/95. Cell growth in M-199 supplemented only with 0.267 units PZI per ml. was rated G/95 on days 4 and 5, G/100 on days 6 and 7, and E/100 on day 8 and thereafter. Cell growth in M-199 supplemented only with 0.267 units per ml. of insulin was rated E/95 on days 5 and 6, and E/100 on day 7 and thereafter. The same amount of insulin supplement with the addition of 2.5 micrograms protamine sulfate per milliliter, was rated G/100 or G-E/100 on days 5–9 and E/100 thereafter. Higher amounts of protamine sulfate did not appear particularly beneficial; concentrations of 5 to 10 micrograms per ml. and the same amount of insulin with 100 percent of surface being covered (E/100 or G/100) only after the tenth day. In a similar operation M-199 plus protamine sulfate alone appeared to be toxic to chick embryo tissue culture cells.

EXAMPLE 3

In carrying out the evaluations of Examples 2, two groups of additional culture bottles were prepared and seeded with cells. The test media employed were (A) M-199 plus 2 percent fetal calf serum and (B) M-199 plus 0.267 units PZI per milliliter. These groups A and B were incubated 24 hours at 37° C., then the test media were removed from the attached cells and replaced with M-199 containing no supplementary serum or PZI. Incubation resumed at 32° C. On the second day after the cells were planted, 24 hours after the medium change, the cells were seeded with rubeola virus, (live, attenuated Schwarz strain). On days 7, 8, 9 and 10, virus was harvested from each bottle of each group. Daily harvests from each group A or B were pooled, and the pooled virus was filtered. For group A, the daily titers were 4.1, 4.4, 4.8 and 5.0. For group B the corresponding daily titers were 3.9, 4.6, 4.6 and 5.5. (Virus titer is expressed as the common, base 10, logarithm of the number of 50% tissue culture infective doses ($TCID_{50}$) per milliliter.

EXAMPLE 4 — LARGE SCALE CELL GROWTH

A protamine zinc insulin (PZI) premix was prepared by adding 20 milliliters of PZI, (100 units per ml.), to 180 milliliters of M-199, and stirring for 2 hours at room temperature, about 25° C. The final concentration of PZI in the pre-mix is thus 10 units per ml.

A chick embryo cell (CEC) concentrate was prepared from 11 day old embryos with trypsinization at 37° C. and washing in M-199. 300 Milliliters of suspension containing about $3.0 \times 10^7$ cells per milliliter were prepared.

The PZI pre-mix, CEC concentrate and M-199 medium were mixed in a series of separate operations in separate 4 liter bulk dispensing containers; then 75 milliliter aliquots from each container were dispensed into 32 fluid ounce glass bottles, and the cells were incubated at 37° C. and observed for cell morphology and percent confluency of the cell sheet. Check operations using M-199 and M-199 plus 2 percent fetal calf serum were also employed. In all cases, the ingredient ratios were selected to provide 1.5 ml. of CEC concentrate ($4.5 \times 10^7$ cells) per 75 ml. bottle, and 1 milliliter of PZI concentrate, (10 units) per 75 ml. bottle, for a final PZI concentration of 0.133 units per milliliter.

With M-199 alone, cell morphology was continuously poor, and confluency increased only from 10 percent on day one to 40 percent on day 4. With M-199 and 2 percent fetal calf serum, morphology was fair on the first day, with 20 percent confluency, increasing to 30–40 percent on day 2 and 60 percent on day 3. Morphology was fair to good by the fourth day and confluency of the cell sheet was 75–85 percent complete. When components were mixed in a 4-liter Pyrex ® glass vessel by first adding the CEC concentrate to the M-199, then adding the PZI pre-mix to the mixture, 75 percent confluency with good cell morphology was observed on the first day after dispensing by gravity. The same rating continued on the second day. Similar results were obtained with pressurized dispensing into the glass culture bottles, and 60 percent confluence with good morphology was obtained in one day after dispensing into Falcon ® plastic bottles.

When the order of adding PZI pre-mix and CEC concentrate was reversed, (PZI before CEC), fair to good morphology with 60 to 70 percent confluence was obtained after one day, with both gravity and pressurized dispensing. By the third day, these tissue culture bottles were evaluated as 70–75 percent confluent with good morphology.

In two other operations, the components were mixed by adding the cells last. In one operation a 4-liter stainless steel vessel was used; in the other, the mixing was done in a Falcon ® plastic vessel. In both cases, fair to good morphology and 45 to 65 percent confluence was evident after one day of incubation.

In other operations chick embryo cells were seeded in a bulk tissue culture propagator having an internal polystyrene sheet in a spiral configuration as the primary cell attachment and growth surface. (Dyna Cell, Cooke Laboratory Products, Alexandria, Virginia) Cells were grown in M-199 containing 0.13 units PZI per milliliter to substantially complete confluency, then seeded with measles virus and incubated with M-199 (without PZI). Virus replication was excellent.

EXAMPLE 5 — MEASLES VIRUS PRODUCTION

For preparation of measles virus vaccine in chick embryo fibroblasts grown in serum-free media, the following are prepared:

A. M-199 Growth Medium — M-199 with Hank's Basal Salt Solution, plus 0.350 gm sodium bicarbonate per liter.

B. M-199 Maintenance Medium — M-199 with HBSS, plus one gram sodium bicarbonate per liter.

C. L-glutamine solution, 10 milligrams — L-glutamine per liter of solution B.

D. Sodium Pyruvate Solution, 5.5 milligrams solution pyruvate per liter of solution B.

E. L-Thyroxine solution, 12.5 micrograms L-thyroxine per liter of solution B.

F. PZI Pre-mix, 10 units protamine zinc insulin per milliliter, prepared as in Example 4.

G. D-Glucose — 20 percent solution in double distilled water, autoclaved at 121° C. for 15 minutes to sterilize.

H. Chick embryo fibroblast suspension in M-199, 2.7 × $10^7$ cells per milliliter.

Three bulk cell suspensions were prepared, and dispensed into 32 fluid ounce glass bottles, as follows:

Bulk suspension No. 1: ("FCS"; fetal calf serum medium) 2450 milliliters of A, with 50 milliliters fetal calf serum, and 60 milliliters of H. Stirred gently for 15 minutes before dispensing.

Bulk suspension No. 2: ("PZI"; protamine zinc insulin medium) 2400 milliliters of A; 18.75 ml. of G; 12.5 ml. of C; 12.5 ml. of D; 60.0 ml. of H and 33.3 ml. of F (PZI pre-mix). Stirred gently 15 minutes before dispensing. The added glucose makes a final glucose concentration of about 0.25 percent by weight.

Bulk suspension No. 3: ("PZIT"; PZI medium with thyroxine) 2400 milliliters of A, 18.75 ml. of G; 12.5 ml. each of C and D; 50.0 ml. of E; 60.0 ml. of H, and 33.3 ml. of F. Stirred gently 15 minutes before dispensing.

The cells were incubated at 37° C. until a 95 to 100 percent confluent cell sheet was obtained in each bottle, 24 hours in all cases. Bottles with bulk suspension No. 1 were seeded with virus after 24 hours; the No. 2 and 3 bottles after 48 hours. Virus seeding was carried out by aspirating the medium off the cell sheet; replacing the medium with 100 milliliters of solution B containing $10^{5.4}$ $TCID_{50}$ of live attenuated measles virus; and incubating the bottles at 32° C. thereafter.

Virus was harvested seven days later, and a second harvest was made from the No. 1 and No. 3 group bottles three days after the first harvest.

EXAMPLE 6

In a procedure similar to that of Example 5, measles virus was propagated in chick embryo fibroblast tissue culture grown in the FCS, PZI and PZIT media. About 95 – 100 percent confluent monolayers were obtained after 48 hours incubation at 36.5° –37° C. At this time, media was removed by aspiration and 100 milliliters of M-199 maintenance medium (solution B of Example 5) was added, together with seed measles virus. The infected bottles were incubated at 32° C. and observed for cytopathic effects and virus titer.

The results of one series of such operations is set out below. Different groups of bottles were infected with different seed measles virus, indicated as $S_1$ and $S_2$ in the table. Titer is expressed as the common, base 10 logarithm of the number of tissue culture infective doses ($TCID_{50}$'s) per 0.5 milliliter. Cytopathic effect, "CPE" is indicated numerically on a scale of 0- no visible effect to 4- cell sheet destroyed. Where two readings are reported on the same day, they were made about 7 hours apart.

TABLE - EXAMPLE 6

| Growth Media | Seed Virus | | 5 days | 6 days | | 7 days | | 8 days | | 9 days | 10 days | 11 days | 12 days |
|---|---|---|---|---|---|---|---|---|---|---|---|---|---|
| FCS | $S_1$ | Titer | 4.6 | 4.5 | 4.7 | 5.0 | 5.0 | 4.7 | 4.5 | 4.5 | | | |
|  |  | CPE | 1− | 1− | 1− | 1− | 1 | 2+ | 3 | 4 | | | |
| FCS | $S_2$ | Titer | 3.8 | 4.3 | 4.5 | 5.5 | 5.1 | 4.7 | 4.6 | 3.8 | | | |
|  |  | CPE | 0 | 1− | 1− | 1 | 1 | 2 | 3 | 4 | | | |
| PZI | $S_1$ | Titer | 3.6 | 4.2 | 4.3 | 5.2 | 5.5 | 5.5 | 5.5 | 5.2 | 5.4 | 5.8 | 5.6 | 5.7 |
|  |  | CPE | 0 | 1− | 1− | 1− | 1− | 1 | 2− | 2 | 3 | 3 | 3 | 4 |
| PZIT | $S_1$ | Titer | 4.8 | 5.4 | 5.5 | 5.7 | | | | | | | | |
|  |  | CPE | 1 | 2 | 3 | 3+ | | | | | | | | |
| PZIT | $S_2$ | Titer | 3.8 | 4.3 | 4.4 | 5.4 | 5.2 | 5.8 | 5.7 | | | | | |
|  |  | CPE | 0 | 1− | 1− | 1−2 | 2 | 3 | 4 | | | | | |

From the above table, it is apparent that the virus vaccine titers obtained with cells grown in the serum free PZI and PZIT media average about one log (tenfold) higher than titers obtained in FCS medium. The table also indicates that the maximum vaccine titers obtained using the serum free media are generally equal to or higher than titers from the FCS system and that the peak titers are generally maintained longer than in the FCS cell system.

EXAMPLE 7

The procedure of Example 6 was repeated using chick embryo fibroblasts from 9 or 11 day old embryos trypsinized 30 minutes at 37° C.; the PZI medium and $S_2$ seed virus of Example 6 and a third seed virus, $S_3$. With the $S_2$ seed and cells from 11 day old embryos, a virus titer of 4.3 was attained on the sixth day and titers of 4.2 – 4.9 were obtained daily through the tenth day. With the $S_3$ seed, titers were between 4.2 and 4.6 from the sixth through the tenth day.

In cells from the 9 day old embryos, the titer with the $S_2$ seed reached 4.4 on the sixth day and titers of 4.8 – 5.3 were obtained on days 7 – 9. On day 12, a titer of 5.2 was obtained, in similar cells, titer from the $S_3$ seed was 4.6 after 5 days, increasing to 5.2 – 5.9 on days 6 and 7, to 6.0 on day 8, when further culture was terminated.

Similar results can be obtained using live mumps virus (Jeryl Lynn strain), instead of measles virus. See U.S. Pat. No. 3,555,149.

EXAMPLE 8

Using the PZI medium as described above, Schwarz strain measles virus was propagated in CEC tissue culture. Three lots, using three lots of seed virus were employed, and samples were taken for analysis of insulin by radioimmunoassay at various stages in the procedure.

The Medium 199 chemically defined maintenance medium, alone or seeded with chick embryo cells, and the seed viruses were all found to contain less than 4 microunits insulin per milliliter. The M-199 containing PZI seeded with chick embryo cells contained about 0.15 units per milliliter which decreased to about 0.07 units per milliliter after 48 hours incubation. For comparison, two lots of fetal bovine serum were found to contain 5.3 and 7.3 microunits per milliliter, while a chemically-undefined medium M-199 plus 2 percent calf serum contained less than 4 microunits per milliliter.

The final harvest vaccines were found to contain about 374, 95 and 357 microunits insulin per milliliter (average of two determinations). At the titers produced, a typical dosage is 0.5 milliliters.

EXAMPLE 9

The invention was employed in production of Rubella virus in duck embryos according to a similar procedure. See U.S. Pat. No. 3,401,084.

Ten day old duck embryos were prepared, trypsinized at 37° for 50 minutes, centrifuged, washed and suspended in M-199 with 0.007 percent added $NaHCO_3$. A PZI medium was prepared using 901 ml. similar M-199, 13 ml of a PZI premix of Example 4; and 61 ml of the cell suspension. The cell and PZI medium suspension were dispensed into 32 fluid ounce glass tissue culture bottles and 75 square centimeter polystyrene tissue culture vessels and incubated at 37° C. At least 75 percent of the cells were observed to have attached to the vessel surface within about 3 hours. In contrast, a control incubation in M-199 plus 2 percent calf serum showed 25 percent attachment at this time.

After 18 hours incubation, the duck embryo cells in the PZI medium showed 80–90 percent confluency with very uniform distribution, and cells in the control, calf serum medium showed 60–70 percent. 42 Hours after planting, the duck embryo cells in PZI medium showed 100 percent confluency. The medium was decanted and replaced with M-199 with Earle's Basal Salt Solution and 2200 milligrams $NaHCO_3$ per liter, pH 7.6. Five bottles were infected with a commercial duck cell adapted HPV-77 strain, passage 5 Rubella virus vaccine (Meruvax ® Merck Sharp & Dohme) and four bottles were seeded with Cendehill strain of Rubella virus vaccine (normally propagated in rabbit kidney tissue culture.

The virus seeding was carried out by reconstituting 5 single dose vials of the lyophilized duck embryo virus in 2.5 ml of maintenance medium and mixing the resulting mixture with 500 ml. of the maintenance medium. 100 Ml. of the virus dilution was used per bottle. Cendehill virus seeding was similarly carried out. Virus was harvested daily from the fourth through the eighth day.

EXAMPLE 10

The medium of the invention was employed in rabbit kidney tissue culture, used in production of the Cendehill strain of live rubella virus vaccine. Kidneys were removed aseptically from 21 day old rabbits, minced, washed in M-199 maintenance medium, trypsinized centrifuged. The centrifuged cells are washed twice in M-199 and suspended in M-199 by conventional procedures.

The cells are seeded in 75 $cm^2$ polystyrene tissue culture bottles at a concentration of about $1.6 \times 10^7$ cells per bottle, with M-199 supplemented with Hank's Balanced Salts and one gram $NaHCO_3$ per liter; with glucose to a final concentration of 2.5 grams per liter; and 28 micrograms sodium pyruvate and 150 micrograms L-glutamine per milliliter. The cell seed suspension in the medium has a final concentration of $5 \times 10^5$ cells per ml. A PZI premix prepared as in Example 4 is added to give a final PZI concentration of 0.13 units per ml.

Cells and medium were incubated at 37° C for 4 days, after which the PZI medium was replaced with the identical maintenance medium without PZI. Maintenance medium was replaced every 2 days thereafter. Full confluence was reached on the fifth day and the cells grown in the PZI medium retained almost pure epithelial appearance even throughout 14 days of tissue culture.

Good yields of rubella virus vaccine can be obtained by growing rabbit kidney cells in tissue culture as described above, decanting the PZI medium after substantially complete confluency is obtained (from about the fourth to seventh day), seeding the cells with live attenuated rubella virus (Cendehill strain); adding replacement maintenance medium and incubating for 3 to 5 days until good virsu proliferation has occurred.

EXAMPLE 11

Chick embryo cells, M-199 and a PZI premix were prepared substantially as described above in Examples 1–4. The cells were planted at a concentration of $6 \times 10^5$ cells per milliliter in M-199 containing a final PZI concentration of 0.133 units per milliliter. 75 Milliliters of the resulting cell suspension were dispensed into each of a series of 32 fluid ounce glass bottles, and incubated for 48–72 hours at 37° C. At this time confluency and morphology were excellent. The bottles were then seeded with live attenuated mumps virus (Jeryl Lynn strain) using 2 milliliters per bottle of a 250 fold dilution in M-199 of seed virus having a titer of about $10^6$ $TCID_{50}$ per 0.5 ml. Virus seeding was carried out directly after removal of PZI medium in one series of bottles, and after removal of PZI medium followed by rinsing the cell monolayer once with about 75 ml. of M-199 (without PZI) in a second series. The infected cells were incubated at 37° C with fresh M-199 (without PZI). Observation of cytopathological effects ("CPE") of mumps virus infection were noted by the fourth day after virus seeding. Virus was harvested on the fourth day, and twice daily until CPE reached a value of 4+ (on a scale from zero to 4+), by collecting the culture medium and replacing it with fresh M-199. Titers range from $10^{5.3} - 10^{6.0}$ TCID$_{50}$ per 0.5 ml. No significant difference appeared between the cells rinsed after PZI medium removal and those seeded without washing or rinsing. Repetitive operations indicate similar results, with three to six harvests per bottle being obtained.

EXAMPLE 12

An operation similar to that of Example 11 was carried out using attenuated measles virus. Similar excellent results were obtained in a series using a washing step before virus seeding and in a series in which washing was omitted.

EXAMPLE 13

African green monkey kidneys were trypsinized at 37° C for 4 hours and planted at a concentration of 3.2 times $10^5$ cells per milliliter in M-199 with 0.13 units PZI per milliliter. The procedure used was similar to that described in Examples 11 and 12. Twenty minutes after dispensing into bottles, microscopic examination indicated that at least 50 percent of the cells were attached to the glass. Incubation was at 37° C. since primary monkey kidney cells are known to be difficult to grow in tissue culture, the M-199 medium with PZI was replaced with fresh M-199 medium and PZI after 48 hours, and again three days later. 95 Percent confluency was observed after eight days incubation, at which time the medium containing PZI was removed. The cells were then seeded with live attenuated polio virus, polio virus (2), 0.4 ml. of seed virus (100-fold dilution) per bottle. The cells and virus were then incubated with 100 milliliters of M-199 (without PZI) at 37° C. for virus propagation and harvest. After 48 hours, titers of 1.75–1.8 times $10^5$ plaque forming units ("PFU") per milliliter were obtained, increasing to $2.3-2.4 \times 10^5$ PFU/ml. after 72 hours incubation.

EXAMPLE 14

In procedures similar to those described above, confluent monolayers of chick embryo cells were grown in M-199 with PZI for three days. The M-199 with PZI was then replaced with M-199 (100 ml. per bottle) and vesicular stomatitis virus ("VSV") 1000 TCID$_{50}$ per bottle. After 20 hours additional incubation at 37° C. extensive virus proliferation was noted by observation of cytopathological effects. CPE was graded at 4 at this time (on a zero to 4+ scale). Cells similarly grown and infected with VSV, but using M-199 plus 2 percent calf serum in lieu of M-199 with PZI, had a CPE grade of 3. Titers of VSV after 20 hours in cells grown in M-199 with PZI were $1.36-2.36 \times 10^6$ PFU/ml.

Other useful illustrative applications of the invention include production of rabies virus in chick embryo cells grown in tissue culture, using a serum free medium (preferably M-199) with PZI (see, U.S. Pat. No. 3,255,080) production of infectious canine hepatitis virus in porcine kidney tissue culture or canine kidney tissue culture (See, U.S. Pat. Nos. 2,915,436 and 3,000,788); production of infectious bovine rhinotracheitis, virus, bovine virus diarrhea virus, and para influenza (PI-3) virus in bovine kidney tissue culture (See U.S. Pat. Nos. 2,941,925; 2,934,473); production of influenza virus in chick embryo tissue culture; and production of rabies virus in bovine kidney tissue culture (See, U.S. Pat. No. 3,585,266).

What is claimed is:

1. In a method which comprises inoculating a chemically defined tissue culture medium with living animal cells and incubating the cells and medium in tissue culture until significant cell growth is obtained, and inoculating the cells with virus, the improvement wherein the incubation is carried out in the presence of a cell growth enhancing amount of protamine zinc insulin U.S.P., B.P. dispersed in said medium; removing the medium containing protamine zinc insulin after significant cell growth is obtained from the cells; replacing said medium with a tissue culture maintenance medium essentially free of protamine zinc insulin; prior to virus innoculation and continuing incubation of the cells in tissue culture.

2. The method of claim 1 wherein the tissue culture medium is a chemically defined maintenance medium.

3. The method of claim 2 wherein the tissue culture medium comprises Medium 199 and is essentially free of detectable protein other than protamine zinc insulin.

4. Method of claim 1 wherein the medium containing protamine zinc insulin is removed and replaced with said maintenance medium within about five days after beginning the incubation.

5. Method of claim 4 wherein the medium containing protamine zinc insulin is removed and replaced within about 48 hours after beginning incubation.

6. Method of claim 4 further comprising the step of washing the cells with maintenance medium essentially free of protamine zinc insulin after removal of the medium containing protamine zinc insulin.

7. Method of claim 4 wherein the medium containing protamine zinc insulin is removed and replaced within about 48 to about 72 hours after beginning incubation, and wherein the cells are primary chick embryo cells.

8. A method which comprises inoculating a tissue culture growth medium with a suspension of living animal cells, said growth medium being an intimate mixture of:
   a. a chemically defined protein-free tissue culture maintenance medium which is adapted to maintain metabolism of said cells but which is insufficient to support growth of said cells into a substantially complete monolayer in tissue culture; and
   b. an amount of from about 0.05 to about 0.5 units per milliliter of protamine zinc insulin U.S.P., B.P. effective to provide an ultimate growth medium adapted to support such growth medium adapted to support such growth of said cells;
and incubating said cells and said growth medium in tissue culture under conditions conducive to growth of a confluent cell monolayer and thereafter inoculating said cells with a virus.

9. In a method which comprises inoculating a tissue culture medium with a suspension of primary living animal cells and incubating the cells and medium in tissue culture until significant cell growth is obtained, prior to virus inoculation, the improvement wherein the medium is Medium 199 having a cell growth enhancing amount of protamine zinc insulin U.S.P., B.P. dispersed therein.

10. A method of claim 9 wherein the cells and medium are incubated under conditions conducive to growth of a confluent cell monolayer.

11. The method of claim 9 further comprising the step of removing the medium containing protamine zinc insulin after significant cell growth is obtained from the cells and within about five days after beginning incubation, replacing said medium with a tissue culture maintenance medium essentially free of protamine zinc insulin;, and continuing incubation of the cells in tissue culture in said maintenance medium.

12. The method of claim 11 wherein the medium containing protamine zinc insulin is removed and replaced with said maintenance medium about 48 hours after beginning incubation.

13. Method of claim 12 wherein the medium containing protamine zinc insulin is removed and replaced about 24 to about 48 hours after beginning incubation.

14. Method of claim 13 further comprising the step of washing the cells with maintenance medium essentially free of protamine zinc insulin after removal of the medium containing protamine zinc insulin.

15. A chemcially defined tissue culture growth medium comprising Medium 199 having a cell growth enhancing amount of from about 0.05 to about 0.5 units of protamine zinc insulin U.S.P., B.P. per milliliter dispersed therein said zinc insulin providing essentially the sole source of detectable insulin activity therein, said medium containing from about 1 to about 2 grams glucose per liter.

* * * * *

UNITED STATES PATENT AND TRADEMARK OFFICE
CERTIFICATE OF CORRECTION

PATENT NO. : 4,072,565

DATED : February 7, 1978

INVENTOR(S) : Stefan Adam Weiss, Harry Lester Torney and William Joseph Caldwell It is certified that error appears in the above-identified patent and that said Letters Patent are hereby corrected as shown below:

Title Page, under "References Cited", second column, second line, "lnfect." should read -- Infect. --;

Title Page, under "References Cited", second column, fifth line, "Giffiths" should read -- Griffiths --;

Column 3, line 21 "enhance cell" should read -- enhance animal cell --;

Column 4, line 24 "buffer" should read -- buffered --;

Column 4, line 24 "USP in injectable" should read -- USP injectable --;

Column 4, line 34 "conductive" should read -- conducive --;

Column 4, line 59 "conductive" should read -- conducive --;

Column 5, line 44 "capable immunizing" should read -- capable of immunizing --;

Column 7, line 53 "5 to 10" should read -- 5 and 10 --;

Column 7, line 61 "Examples 2" should read -- Example 2 --;

UNITED STATES PATENT AND TRADEMARK OFFICE
CERTIFICATE OF CORRECTION

PATENT NO. : 4,072,565

DATED : February 7, 1978

INVENTOR(S) : Stefan Adam Weiss, Harry Lester Torney and William Joseph Caldwell It is certified that error appears in the above-identified patent and that said Letters Patent are hereby corrected as shown below:

Columns 9 and 10, TABLE - EXAMPLE 6, the third line of the Table has been omitted. Please insert the following:

| Growth Media | Seed Virus | | 5 days | 6 days | | 7 days | | 8 days | |
|---|---|---|---|---|---|---|---|---|---|
| PZI | $S_1$ | Titer | 4.7 | 5.4 | 5.6 | 5.9 | 6.4 | 6.3 | 6.4 |
|  |  | CPE | 1- | 1 | 2 | 2 | 3 | 3 | 4 |

Column 9, TABLE - EXAMPLE 6, third line of Table under "Seed Virus", "$S_1$" should read -- $S_2$ --;

Column 12, line 2 "ture" should read -- ture). --;

Column 12, line 46 "virsu" should read -- virus --;

Column 14, line 6 "tissure" should read -- tissue --;

Column 14, line 64 "10. A method" should read -- 10. The method --;

UNITED STATES PATENT AND TRADEMARK OFFICE
CERTIFICATE OF CORRECTION

PATENT NO. : 4,072,565

DATED : February 7, 1978

INVENTOR(S) : Stefan Adam Weiss, Harry Lester Torney and William Joseph Caldwell It is certified that error appears in the above–identified patent and that said Letters Patent are hereby corrected as shown below:

Column 15, line 5 "lin;," should read -- lin; --;

Column 16, line 5 "chemcially" should read -- chemically --.

Signed and Sealed this

Twenty-first Day of November 1978

[SEAL]

Attest:

RUTH C. MASON
Attesting Officer

DONALD W. BANNER
Commissioner of Patents and Trademarks